US008229532B2

(12) United States Patent
Davis

(10) Patent No.: US 8,229,532 B2
(45) Date of Patent: Jul. 24, 2012

(54) EXTERNAL EAR-PLACED NON-INVASIVE PHYSIOLOGICAL SENSOR

(75) Inventor: Daniel Davis, Cardiff, CA (US)

(73) Assignee: The Regents of the University of California, Oakland, CA (US)

( * ) Notice: Subject to any disclaimer, the term of this patent is extended or adjusted under 35 U.S.C. 154(b) by 621 days.

(21) Appl. No.: 12/434,060

(22) Filed: May 1, 2009

(65) Prior Publication Data
US 2009/0275813 A1 Nov. 5, 2009

Related U.S. Application Data

(60) Provisional application No. 61/050,085, filed on May 2, 2008.

(51) Int. Cl.
*A61B 5/1455* (2006.01)
(52) U.S. Cl. ........................................ 600/344; 600/310
(58) Field of Classification Search ........... 600/309–344
See application file for complete search history.

(56) References Cited

U.S. PATENT DOCUMENTS

| | | | |
|---|---|---|---|
| 5,551,423 | A | 9/1996 | Sugiura |
| 5,666,952 | A | 9/1997 | Fuse et al. |
| 5,957,840 | A | 9/1999 | Terasawa et al. |
| 7,263,396 | B2 | 8/2007 | Chen et al. |

OTHER PUBLICATIONS

International Search Report dated Jun. 25, 2009.
Barton et al., A novel method of evaluating the impact of secondary brain insults on functional outcomes in traumatic brain-injured patients, *Acad Emerg Med.*, 2005, vol. 12, pp. 1-6.
Bebout et al., Site dependent differences in the time to detect changes in saturation during low perfusion, *Crit Care Med.*, 2001, vol. 29 No. 12, A115.
Davis et al., Hyperventilation following aero-medical rapid sequence intubation may be a deliberate response to hypoxemia, *Resuscitation*, 2007.
Davis et al., The impact of hypoxia and hyperventilation on outcome following paramedic rapid sequence intubation of patients with severe traumatic brain injury, *Journal of Trauma*, 2004, vol. 57, pp. 1-10.
Dunford et al., Incidence of transient hypoxia and pulse rate reactivity during paramedic rapid sequence intubation, *Annals of Emergency Medicine*, 2003, vol. 42 No. 6, pp. 721-728.
Kawagishi et al., A comparison of the failure times of pulse oximeters during blood pressure cuff-induced hypoperfusion in volunteers, *Anesth Analg.*, 2004, vol. 99, pp. 793-796.
Macleod et al., The desaturation response time of finger pulse oximeters during mild hypothermia, *Anaesthesia*, 2005, vol. 60, pp. 65-71.
Manley et al., Hypotension, hypoxia, and head injury: frequency, duration, and consequences, *Archives of Surgery*, 2001, vol. 136 No. 10, pp. 1118-1123.
Nishiyama, Pulse oximeters demonstrate different responses during hypothermia and changes in perfusion, *Can J Anaesth*, 2006, vol. 53 No. 2, 136-138.
Nuhr et al. Forehead SpO2 monitoring compared to finger SpO2 recording in emergency transport, *Anaesthesia*, 2004, vol. 59, pp. 390-393.
Omert et al., Role of the emergency medicine physician in airway management of the trauma patient. *J Trauma*. 2001, vol. 51 No. 6, pp. 1065-1068.

(Continued)

*Primary Examiner* — Eric Winakur
*Assistant Examiner* — Marjan Fardanesh
(74) *Attorney, Agent, or Firm* — Shimokaji & Assoc, PC

(57) ABSTRACT

In one embodiment, a non-invasive physiological sensor assembly is capable of attachment to a tissue site of the ear comprising of cartilaginous structures of the ear, providing low latency of physiological measurements as well as a secure attachment.

10 Claims, 12 Drawing Sheets

OTHER PUBLICATIONS

Schallom et al., Comparison of forehead and digit oximetry in surgical/trauma patients at risk for decreased peripheral perfusion, *Heart & Lung*, 2007, vol. 36, pp. 188-194.

Severinghaus et al., Errors in 14 pulse oximeters during profound hypoxia, *J Clin Monitoring*, 1989, vol. 5, pp. 72-81.

Tiamfook-Morgan et al., What happens to SpO2 during air medical crew intubations? *Prehosp Emerg Care*, 2006, vol. 10 No. 3, pp. 363-368.

Trivedi et al., Pulse oximeter performance during desaturation and resaturation: a comparison of seven models, J Clin Anesth, 1997, vol. 9, 184-188.

Van De Louw et al. Accuracy of pulse oximetry in the intensive care unit, *Intensive Care Med.*, 2001, vol. 27, pp. 1606-1613.

Walls, Rapid-sequence intubation in head trauma, *Annals of Emergency Medicine*, 1993, vol. 22 No. 6, pp. 1008-1013.

Wang et al., Multivariate predictors of failed prehospital endotracheal intubation, *Acad Emerg Med.*, 2003, vol. 10 No. 7, pp. 717-724.

| Parameter | Mean or % (95% Confidence Intervals) |
|---|---|
| Age (years) 36 | (29-43) |
| Gender (% male) 73 | (57-86) |
| Trauma (%) 83 | (68-93) |
| SBP ≤90 mmHg (%) 16 | (5-33) |
| Indication for Intubation (%)<br>   Respiratory failure<br><br>   Airway trauma<br><br>   Altered level of consciousness | <br>32<br>(18-48)<br>10<br>(3-23)<br>59<br>(42-74) |

FIG. 8

EXTERNAL EAR-PLACED NON-INVASIVE PHYSIOLOGICAL SENSOR

CROSS-REFERENCE TO RELATED APPLICATIONS

The present application claims the benefit under 35 U.S.C. 119(c) to U.S. Provisional Application No. 61/050,085, filed May 2, 2008, titled, "EXTERNAL EAR-PLACED PULSE OXIMETRY PROBE" which is hereby incorporated by reference in its entirety, including specifically but not limited to the systems and methods relating to an external ear-placed non-invasive physiological sensor.

FIELD OF THE DISCLOSURE

The present disclosure generally relates to apparatus and methods for non-invasive physiological sensors, and more specifically to methods and apparatus for external measurement with an ear-placed non-invasive physiological sensor.

BACKGROUND OF THE DISCLOSURE

Non-invasive physiological sensors are applied to the body for monitoring or making measurements indicative of a patient's health. One application for a non-invasive physiological sensor is pulse oximetry, which provides a noninvasive procedure for measuring the oxygen status of circulating blood. Oximetry has gained rapid acceptance in a wide variety of medical applications, including surgical wards, intensive care and neonatal units, general wards, and home care and physical training. A pulse oximetry system generally includes a patient monitor, a communications medium such as a cable, and a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and pulse rate.

SUMMARY OF THE DISCLOSURE

Optical sensors are widely used across clinical settings, such as operating rooms, emergency rooms, post anesthesia care units, critical care units, outpatient surgery and physiological labs, to name a few. Studies have suggested that conditions producing peripheral vasoconstriction, such as decreased ambient temperature or hypoperfusion states, can cause delays of accuracy up to 120 seconds in measurements made by the sensors. In some settings, such as monitoring the oxygenation status of a patient during rapid sequence intubation (RSI), some clinicians prefer a reading that more quickly tracks to the saturation of the core arteries of the brain. An embodiment of the present disclosure to reduce latency in the accuracy of the monitored data of the patient, in particular to reduce such latency in emergency medical services environments is disclosed.

Often, caregivers place optical sensors on the fingers, forehead, earlobe, cheek or nose of a monitored patient. In some cases, these locations may be impractical for pre-hospital or emergency use and/or utilize tissue that may be underperfused, in particular during vasoconstriction and/or hypoperfusion conditions.

It is therefore desirable to provide a sensor assembly, capable of placement at a tissue site that provides a faster response to central changes in oxygenation. It is also desirable for the sensor to have a physiological sensor assembly with a secure attachment at the tissue site. Accordingly, an embodiment of the disclosure includes a non-invasive physiological sensor assembly capable of attachment to a tissue site of the ear, including cartilaginous structures, providing low latency of measurements and/or a secure attachment.

For purposes of summarizing embodiments of the disclosure, certain aspects, advantages and novel features of embodiments of the disclosure have been described herein. Of course, it is to be understood that not necessarily all such aspects, advantages or features will be embodied in any particular embodiment.

BRIEF DESCRIPTION OF THE DRAWINGS

FIG. 8 is a table illustrating exemplary results of a physiological study.

DETAILED DESCRIPTION OF THE PREFERRED EMBODIMENT

Figure 1A:
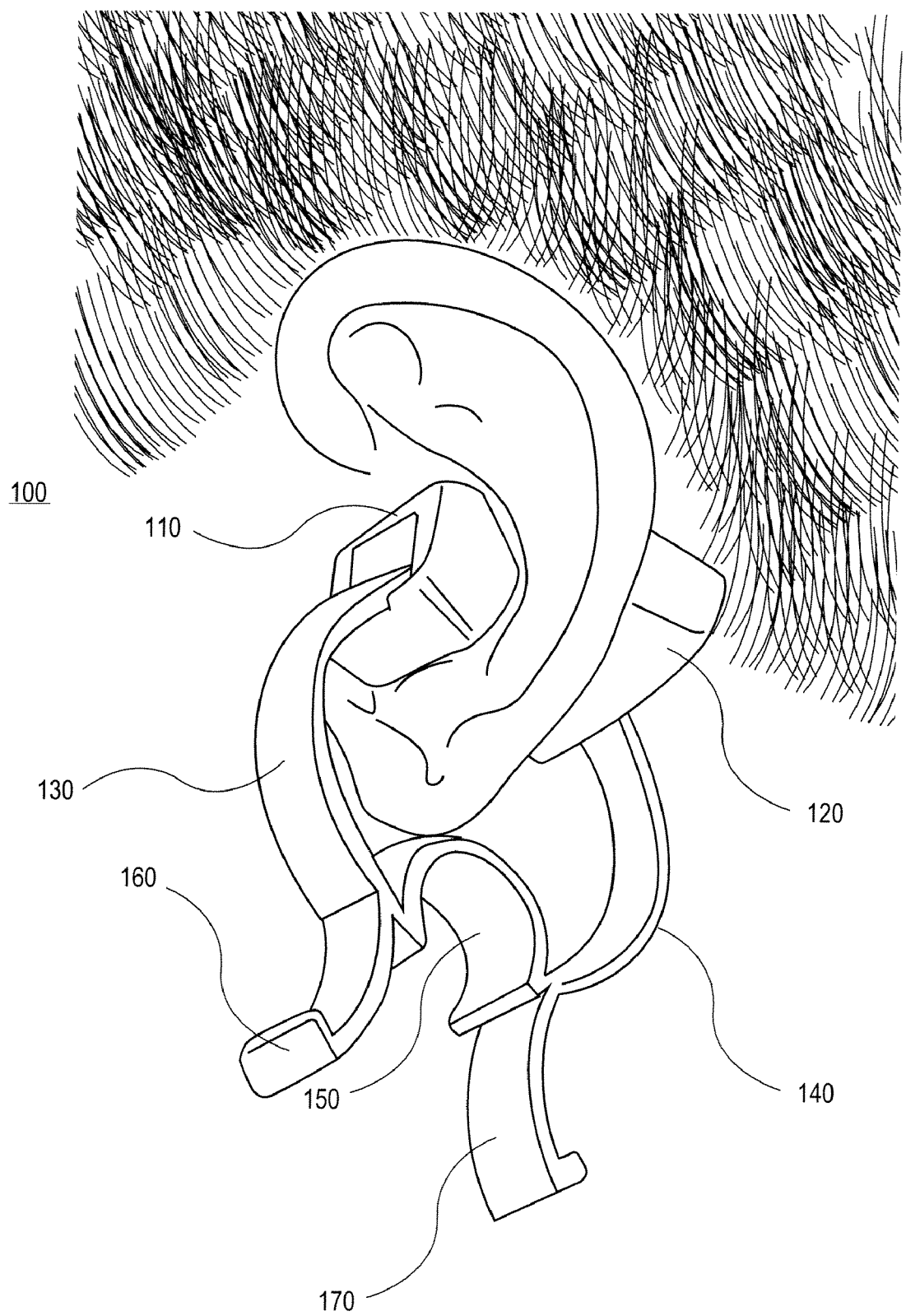
FIG. 1A illustrates a perspective view of an exemplary ear sensor assembly according to an embodiment of the disclosure attached to an ear measurement location.
Figure 1B:
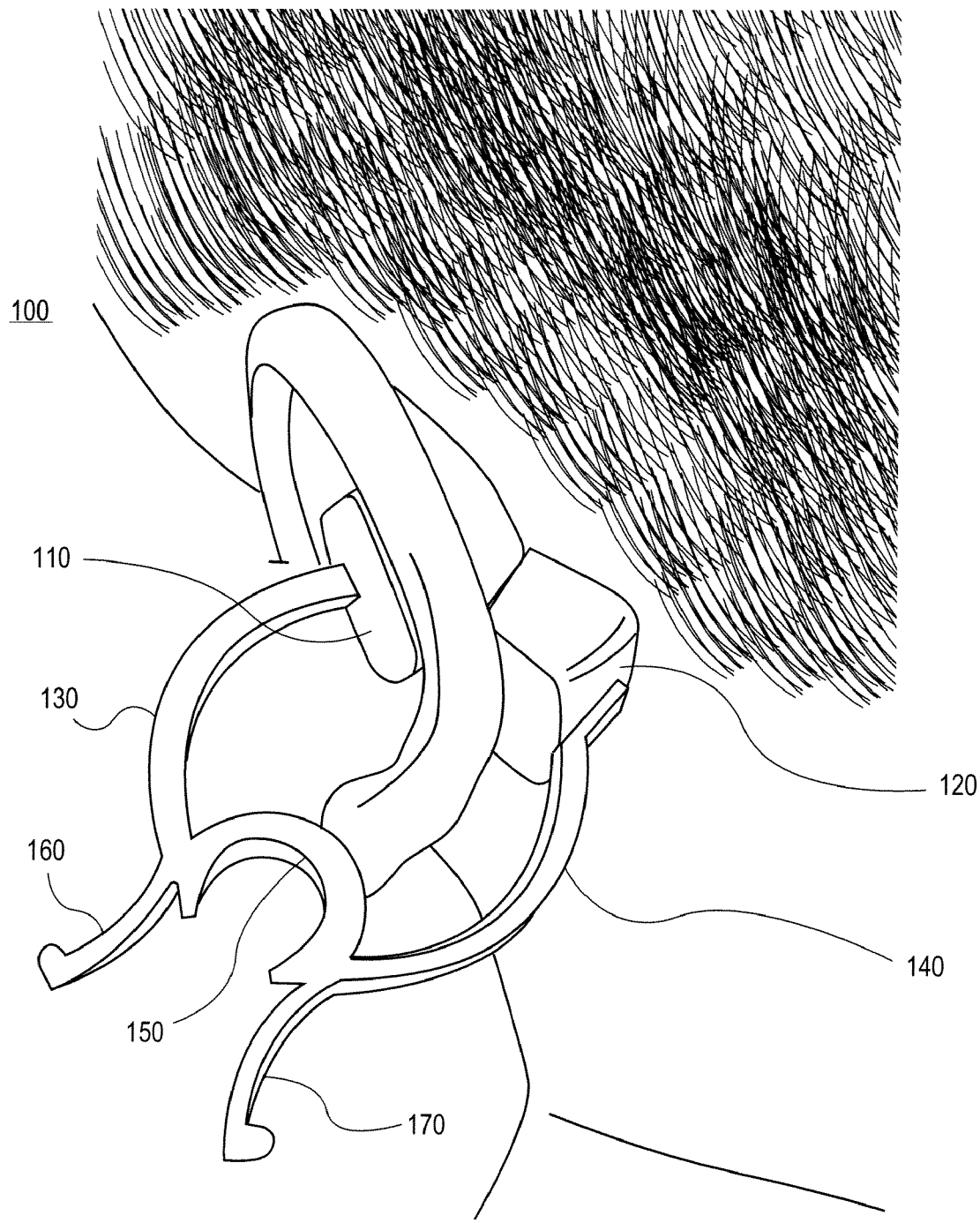
FIG. 1B illustrates a corresponding rear view of the exemplary ear sensor assembly of FIG. 1A.

FIG. 1A is a perspective view of an exemplary ear-placed non-invasive physiological sensor assembly 100 according to an embodiment of the disclosure. FIG. 1B is the corresponding rear view of the exemplary ear sensor assembly of FIG. 1A. The ear sensor 100 can be a clip-type sensor comprising sensor probes 110, 120, an upper clip arm 130, a lower clip arm 140 and a hinge element 150. Sensor probes 110, 120 can be located at the distal end of the upper and lower clip arms 130, 140. The sensor probes 110, 120 may house one or more light emitters and a detector of a pulse oximeter sensor, such as one or more LEDs and a light sensor. Either sensor probe 110, 120 may contain the emitter or the detector. In an embodiment, the emitter opposes the detector such that light emitted by the emitter impinges the tissue, is attenuated thereby, and the attenuated light then impinges the detector. The sensor 100 can be connected to a patient monitor (not shown) via a cable (not shown). For example, the detector outputs a signal to the monitor over the cable which then processes the signal to provide a numerical readout of physiological parameters such as oxygen saturation (SpO2) and pulse rate. In one embodiment, the cable attaches a sensor probe 110, 120 to the patient monitor. One or more wires (not shown) can connect the inner sensor probe 110 to the outer sensor probe 120. The cable and/or wires can be attached to the clip arms 130, 140, housed within the clip arms 130, 140, and/or unconnected to the clip arms.

The sensor 100 can be placed on the ear by applying pressure on the proximal ends 160, 170 of the upper and lower clip arms 130, 140 forming an opening capable of receiving a tissue site between the sensor probes 110, 120. Once the tissue site is inserted into the opening, the pressure on the ends 160, 170 can be released such that the upper (or inner) and lower (or outer) sensor probes 110, 120 come in contact with and substantially secure the assembly 100 to the tissue site, allowing for accurate non-invasive physiological measurement. The sensor probes 110, 120 may be shaped to conform to the cartilaginous structures of the ear, such that the cartilaginous structures can provide additional support to the sensor probes 110, 120, providing a more secure connection, which can be beneficial for monitoring during pre-hospital and emergency use where the patient may move or be moved. For example, the inner sensor probe 110 can be shaped for insertion into the concha of the external ear, near the external canal. As will be understood by one skilled in the art, the concha includes its broad ordinary meaning that includes a hollow defined by the cartilaginous structures of the external ear. The surrounding cartilaginous structures can serve to restrict and hold in place the inner sensor probe 110. The outer sensor probe 120 can be shaped for placement behind the external ear, opposite the inner sensor probe 110. The inner and outer sensor probes 110, 120 may be positioned to align the emitters and detector. The upper and lower clip arms 130, 140 can be outwardly curved away from the ear to reduce contact with parts of the ear other than the contact points for the sensor probes 110, 120. This can create a more secure attachment to the tissue site, reduce patient discomfort, and/or allow better contact with the contact points, thereby providing a more accurate non-invasive physiological measurement.

Although disclosed with reference to the sensor of FIG. 1A and FIG. 1B, an artisan will recognize from the disclosure herein a wide variety of oximeter sensors, optical sensors, noninvasive sensors, medical sensors, or the like that may benefit from the ear sensor disclosed herein, such as, for example, CO2, near infrared spectroscopy (NIRS), lactate/pyruvate, and/or perfusion sensors. Size adjustments of the sensor probes 110, 120 may be made to adjust the probe to any size ear, including sizes designed for pediatric applications. The sensor probes 110, 120 may be detachable from the clip arms 130, 140. The sensor probes 110, 120 may be designed as disposable or reusable probes. The upper and lower clip arms 130, 140 can be housings housing electrical and/or optical components of the non-invasive physiological sensor 100. The cable can be connected to the inner sensor probe 110, the outer sensor probe 120, or cables can connect both sensors 110, 120 to the monitor. In addition, the ear sensor 100 may be used with a portable monitor. Such monitors can be integrated into a hand-held device such as a PDA and may not include cables or separate monitors and/or may also include memory or other electronic devises usable by a monitor to, for example, configure itself and/or provide quality control.

The location of the sensor probes 110, 120 in relation to the external ear, as illustrated in FIG. 1A and FIG. 1B can allow measurement on a portion of the ear that maintains good perfusion, even with cold temperature or patient hypotension. This may prevent loss of signal due to sluggish flow through the tissue which can lead to a lag or latent period in the reported measurement. For example, measuring at the concha can provide better measurements than measuring at the earlobe due to better profusion and less sluggish flow.

COMPARATIVE EXAMPLE

The study below describes a comparative example, showing latency and loss of pulse oximetry signal with the use of digital (that is, attached to a digit) probes during pre-hospital rapid sequence intubation (RSI). This comparative shows just one aspect where embodiments of the disclosure may be beneficial.

Methods

Design

This was a secondary analysis of the air medical RSI database, which included prospectively collected physiological data.

Setting

At the time of this investigation, Mercy Air Medical Service included twelve bases throughout Southern California and Nevada. Data for this analysis were obtained from the eight bases in California. Crew configuration included flight nurses and a paramedic. Crews respond to scene calls at the discretion of ground providers and perform a variety of advanced procedures, including RSI. The average number of RSI procedures is approximately 2.5/base/month.

Subjects

All patients undergoing air medical RSI for whom physiological data were available were eligible for inclusion in this analysis. Patients treated between July 2006 and June 2007 were eligible.

Protocol

The RSI protocol during the study period included the following: passive preoxygenation with supplemental oxygen via nonrebreather mask for about 1 to about 3 min, premedication with lidocaine (about 1.0 to about 1.5 mg/kg i.v.) with suspected brain injury, etomidate (about 0.3 mg/kg i.v. to a maximum of about 20 mg i.v.), and succinylcholine (about 1.5 mg/kg i.v.). Midazolam (about 2 to about 5 mg/kg i.v.) and vecuronium (about 0.1 mg/kg i.v.) were administered following endotracheal tube confirmation. Monitoring of patients undergoing RSI was performed with a hand-held oximeter-capnometer. These devices include a non-disposable digital (applied to a digit) probe. Commercially available, disposable, adhesive digital probes were also available for use at the discretion of air medical crews. Data from the oximeter-capnometer devices are stored in 8-second intervals and can be exported for analysis. At the time of data collection for this analysis, air medical crews routinely utilized qualitative capnometry for initial confirmation of endotracheal tube placement followed by use of digital capnometry. Since that time, crews have been encouraged to utilize digital capnometry for initial confirmation.

Data Analysis

Data from the oximeter-capnometer devices was exported into a software program that displays physiological data, such as, for example, SpO2, heart rate, end-tidal carbon dioxide (EtCO2), and/or ventilation rate, graphically and allows the time and absolute value for each stored data point to be determined. Clinical data were abstracted from the electronic patient care record. The first objective was to define the incidence of SpO2 latency. Multiple SpO2 probes were not used simultaneous by the air medical crews. Patients in whom oxygen desaturation occurred during the RSI procedure were identified, as this resulted in a defined decrease in SpO2 during apnea followed by rapid correction after intubation. An oxygen desaturation was defined as a decrease in SpO2 to about 93% or less or a continued decrease in SpO2 if the initial SpO2 was already about 93% or less. The emergence of EtCO2/ventilation data was used to define successful intubation.

Because air medical crews routinely used qualitative capnometry during the study period, manikin simulators were utilized to determine the average amount of time required to confirm endotracheal tube placement prior to placement of the digital capnometry probe (37 seconds). Latency was determined if the lowest recorded SpO2 value during a desaturation occurred after intubation, defined as a period starting about 37 seconds before until about 2 min after the emergence of EtCO2/ventilation data. The second objective was to define the incidence of loss of SpO2 signal during the RSI procedure. This was defined by an absence of SpO2 data for at least about 30 seconds during a period from about 3 minutes before to about 3 minutes after the appearance of EtCO2/ventilation data. All data were presented descriptively, with 95% confidence intervals or 25th-75th quartiles used where appropriate.

Results

Physiological RSI data were available for a total of 210 patients undergoing air medical RSI over the 12-month study period. The data demonstrated a latent period and loss of SpO2 signal during the RSI period. Of the 210 total patients, 86 were excluded due to the absence of pre-intubation data. Clinical and demographic data for the remaining 124 patients are displayed in Table 1. Of these, 98 (79%) had loss of SpO2 signal for at least 30 seconds during the RSI period.

Adequate data to determine the presence of oxygen desaturation during RSI were available for 110 patients. Of these, 49 had a desaturation event (45%). The mean and median for lowest recorded SpO2 value were 76% (95% CI 72-79%) and 76% (25th-75th quartiles 64-86%), respectively. The mean and median duration for the desaturation (total time ≦93%) were 259 sec (95% CI 142-379 sec) and 176 sec (25th-75th quartiles 56-358 sec), respectively. Of the 49 patients with oxygen desaturation, 13 (27%) became tachycardic (heart rate >100 beats per min) and 12 (24%) became bradycardic (heart rate <60 beats per min) during the episode. Latency was observed in 27 of the 49 patients with oxygen desaturation (55%). Even if the 37-second time period prior to emergence of EtCO2 and ventilation data were eliminated, 23 of the 49 patients (47%) would have met criteria for a latency period.

Discussion

A high incidence of pulse oximetry signal latency associated with desaturations during pre-hospital RSI with use of digital SpO2 probes may be documented. There are high incidences of desaturations with pre-hospital RSI and the increasing velocity of desaturation as the SpO2 decreases below 94%. These data are consistent with previously published reports, although this appears to be early documentation of pulse oximetry latency in the pre-hospital environment. In addition, loss of the pulse oximetry signal during RSI periods appears to occur in the majority of cases. These data may partially account for the high rate of desaturation associated with pre-hospital RSI. Desaturation during emergency RSI in the in-hospital setting has been reported in less than one-third of all cases, rates reported with pre-hospital RSI have generally been much higher. Although the use of digital probes is also widespread in the inpatient setting, pre-hospital patients may be more likely to suffer digital hypoperfusion, either as a result of pre-resuscitation hypotension or lower ambient temperatures.

The etiology of both pulse oximetry latency and loss of signal appear to be related primarily to the site at which the sensor is placed. While digital SpO2 probes are ubiquitous, perfusion to the digits is extremely sensitive to changes in hemodynamic status, arm position, and temperature. In the anesthesia literature, the validity with regard to "real time" accuracy has demonstrated to be negatively affected by two factors: mild hypothermia (core body temperature about 35 to about 36 C) and the presence of vasoactive drugs.

Alternative sites for obtaining SpO2 values based on performance characteristics may offer potentially lesser latency. For example, centrally placed SpO2 probes, such as those according to embodiments of the disclosure, may provide more timely information for patients undergoing pre-hospital RSI or other procedures. Some clinicians may prefer a reading that more quickly tracks to the saturation of the core arteries at the brain.

The main limitation to this study was the use of a definition for latency, since multiple probes were not used simultaneously and because the exact moment of intubation could not be determined. However, even use of a conservative definition resulted in nearly half of all cases demonstrating SpO2 latency. In addition, one could not be sure that this phenomenon is related specifically to probe site, although the existing literature supports this concept. Finally, the incorporation of patient variables, preoxygenation strategy, or number of intubation attempts was not attempted to be included into the analysis.

The comparative example documents incidences of SpO2 signal latency and signal loss during pre-hospital RSI with use of digital probes. This is likely related to the site, such as fingers or toes, at which the sensor is placed. Embodiments of the disclosure may provide relatively faster response to central changes in oxygenation while also substantially removably securing the sensor assembly to the tissue site.

Figure 2A:
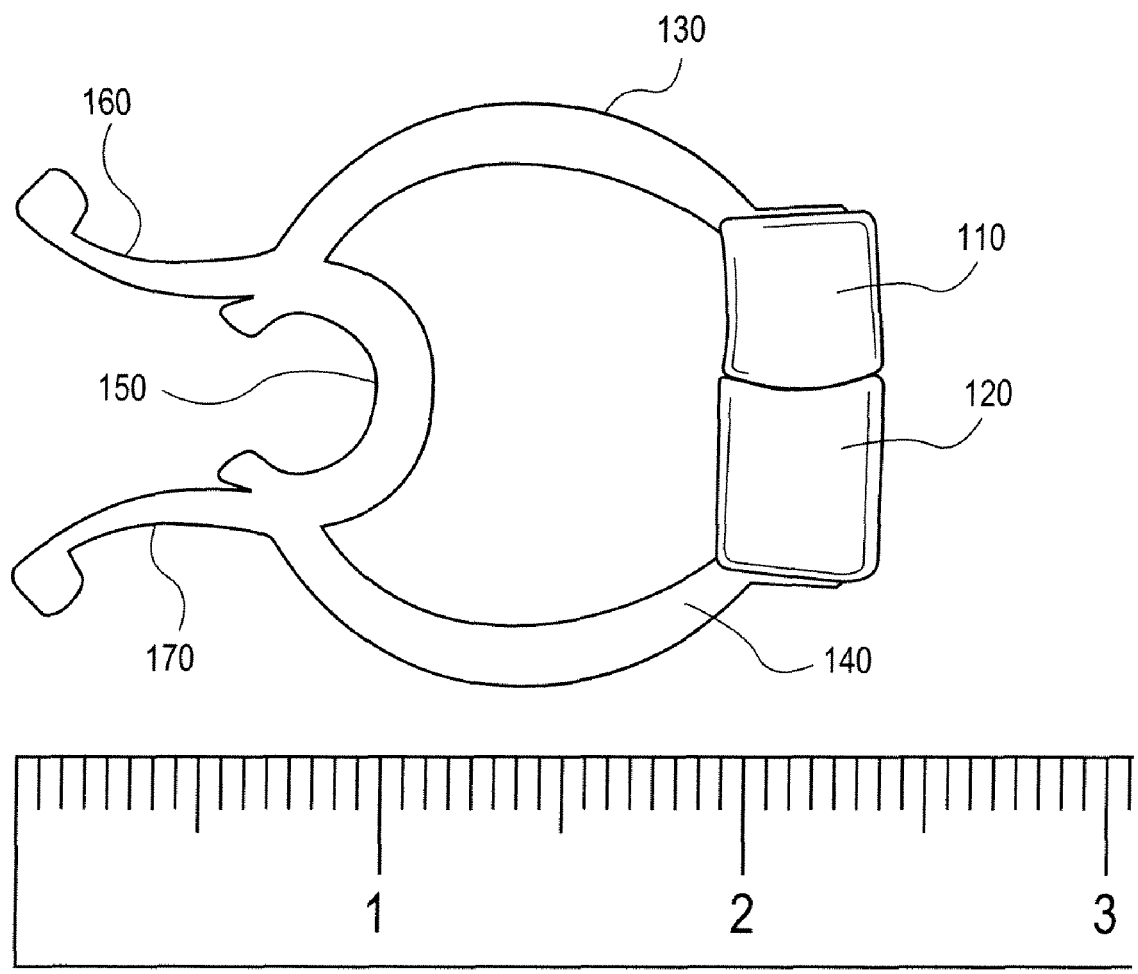
FIGS. 2A-C illustrate side hinged-closed, front hinged-closed and bottom-right hinged-open perspective, respectively, of embodiments of the exemplary ear sensor assembly of FIG. 1A.
Figure 2B:
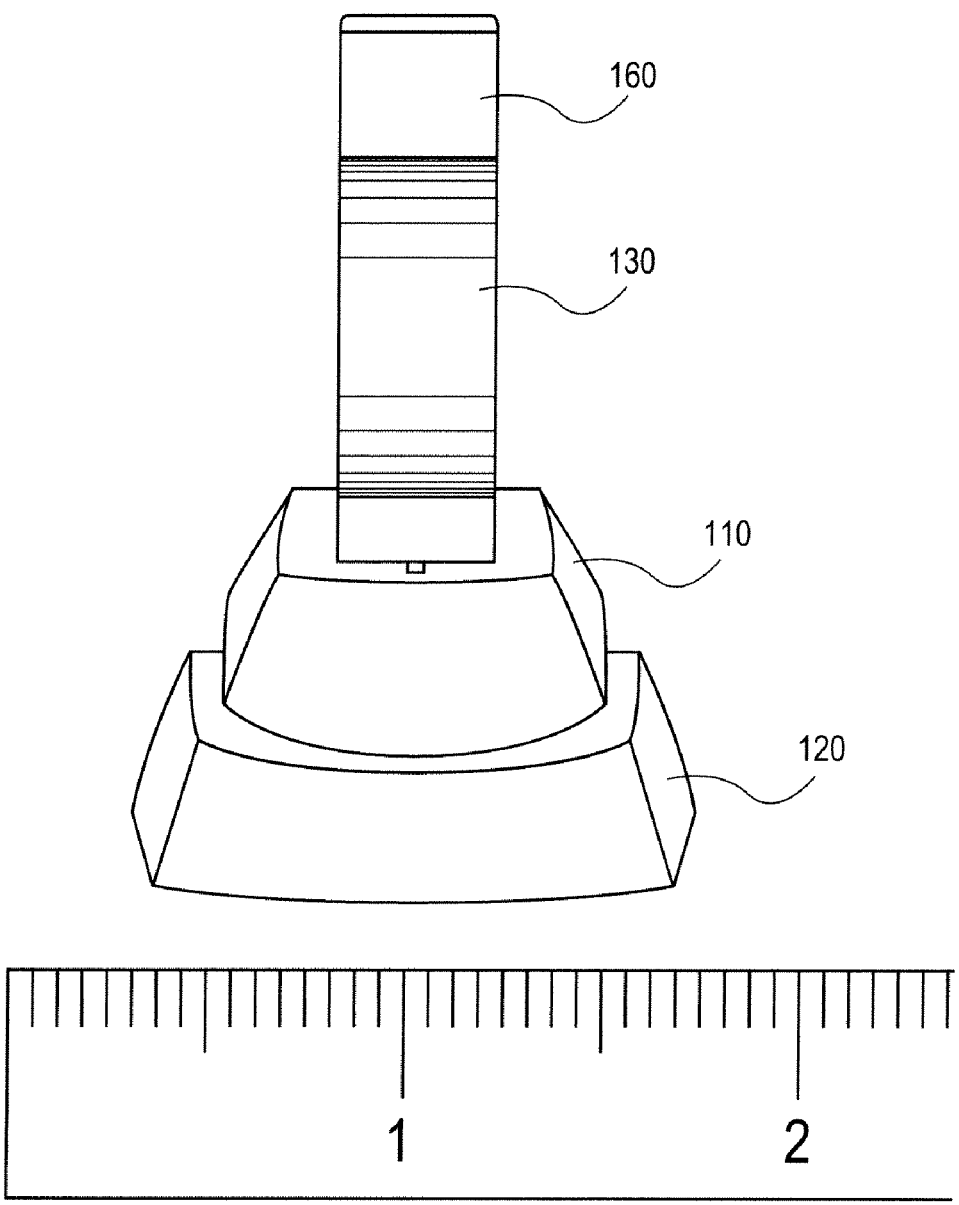
Figure 2C:
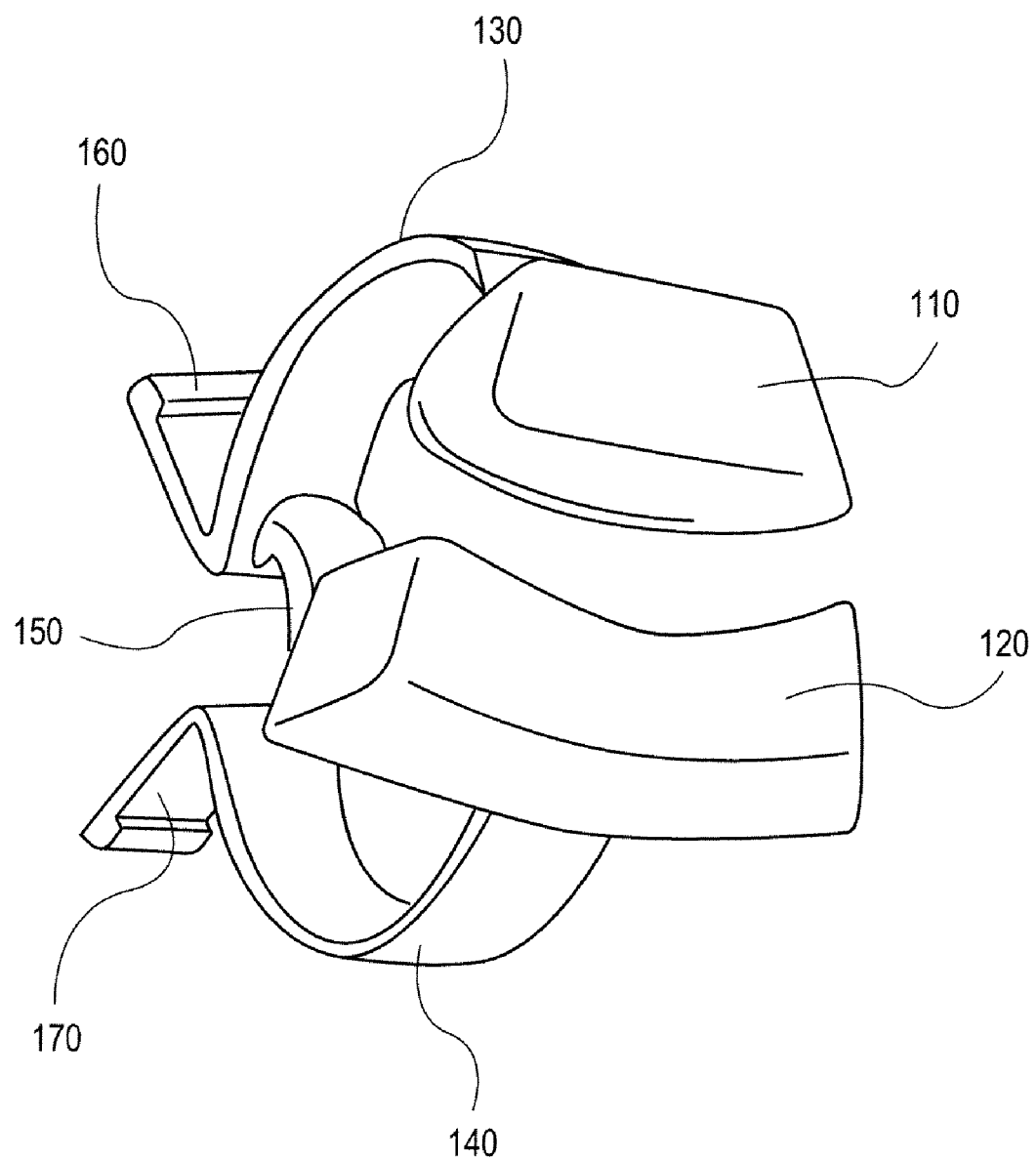

FIGS. 2A-C are side hinged-closed, front hinged-closed and bottom-right hinged-open perspectives, respectively, of the exemplary ear sensor assembly of FIG. 1A. As discussed above, the inner sensor probe 110 and outer sensor probe 120 may be separated about the hinge element 150 by applying pressure to the ends 160, 170, such that the opening between the probes 110 and 120 becomes large enough to fit the tissue site. Once the sensor 100 is placed about the tissue site, the upper and lower ends 160, 170 can be released, permitting the probes 110 and 120 to come into contact with and releasably attach to the ear. In the illustrated embodiment, the hinge element 150 is a flexible hinge but an artisan will recognize from the disclosure herein that a wide variety of hinge types may be used, such as a spring hinge. As shown by FIGS. 2A-C, the inner and outer sensor probes 110, 120 of the illustrated embodiments are asymmetric. The smaller inner sensor probe 110 is configured to conform to the cartilaginous structures of the ear, such as by placement within the concha of the external ear. Meanwhile the larger outer sensor probe 120 is configured for placement behind the external ear. The larger outer sensor probe 120 can provide a greater contact area with the external ear, improving the quality of measurements and/or providing a more secure attachment through increased frictional engagement. In other embodiments, the sensor probes may be symmetrical. In the illustrated embodiment of FIG. 2A, the length of the sensor assembly 100 is about 2 inches to 3 inches or about 5.1 cm to about 7.6 cm. In some embodiments, the sensor assembly may be smaller than 2 inches (5.1 cm) or may be greater than 3 inches (7.6 cm) depending on the size of the ear to which the sensor is attached.

Figure 3:
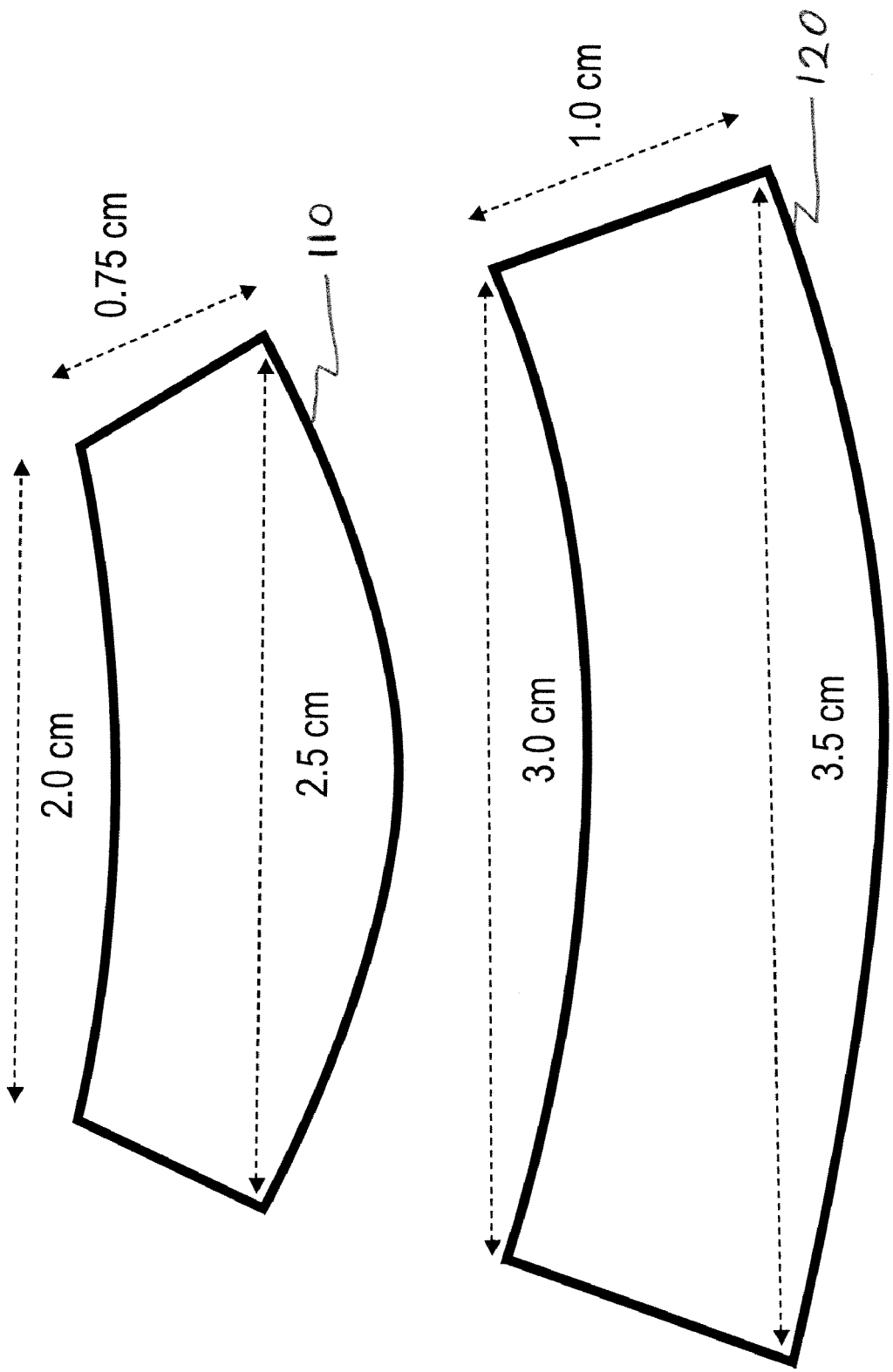
FIG. 3 illustrates a simplified front perspective view of a block diagram of the inner and outer sensor probes of the ear sensor assembly of FIG. 1A.

FIG. 3 illustrates a simplified front perspective view of a block diagram of the inner and outer sensor probes 110, 120 of the ear sensor assembly of FIG. 1A. The width of the inner sensor probe 110 is about 2.0 cm at the top and about 2.5 cm at the contact point. The outer sensor probe 120 is about 3.5 cm at bottom and about 3.0 cm at the contact point. The range of widths for the inner and outer sensor probes can vary from about 2.0 cm or smaller to about 3.5 cm or larger in order to fit in ears of various sizes, including smaller sizes for pediatric applications. In the illustrated embodiment of FIG. 3, the inner sensor probe has a convex contact point while the outer sensor probe has a concave contact point for a more advantageous fit within the outer ear and without the outer ear, respectively. In other embodiments, other shapes can be used for a better fit with the cartilaginous structures of the ear.

Figure 4:
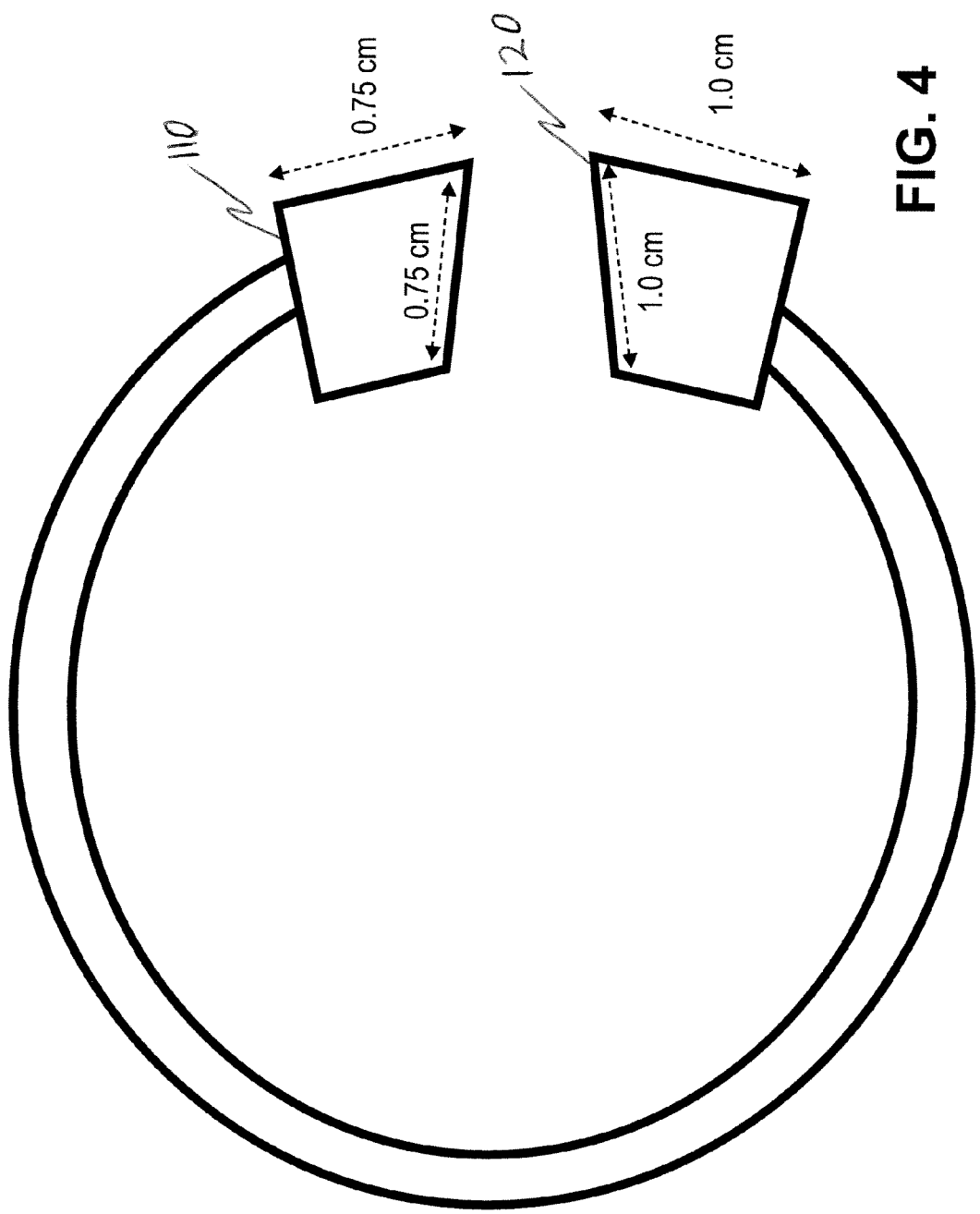
FIG. 4 illustrates a simplified side perspective view of a block diagram of the sensor assembly of FIG. 1A.

FIG. 4 illustrates a simplified side perspective view of a block diagram of the sensor assembly 100 of FIG. 1A. In the illustrated embodiment, the inner sensor probe 110 has a depth and height of about 0.75 cm. The outer sensor probe 120 has a depth and height of about 1.0 cm. The range of depths and heights for the inner and outer sensor probes can vary from about 0.75 cm or smaller to about 1.0 cm or larger in order to fit ears of various sizes. In other embodiments, the height and depth of the sensor probes can differ from each other for a better fit with the ear.

Figure 5A:
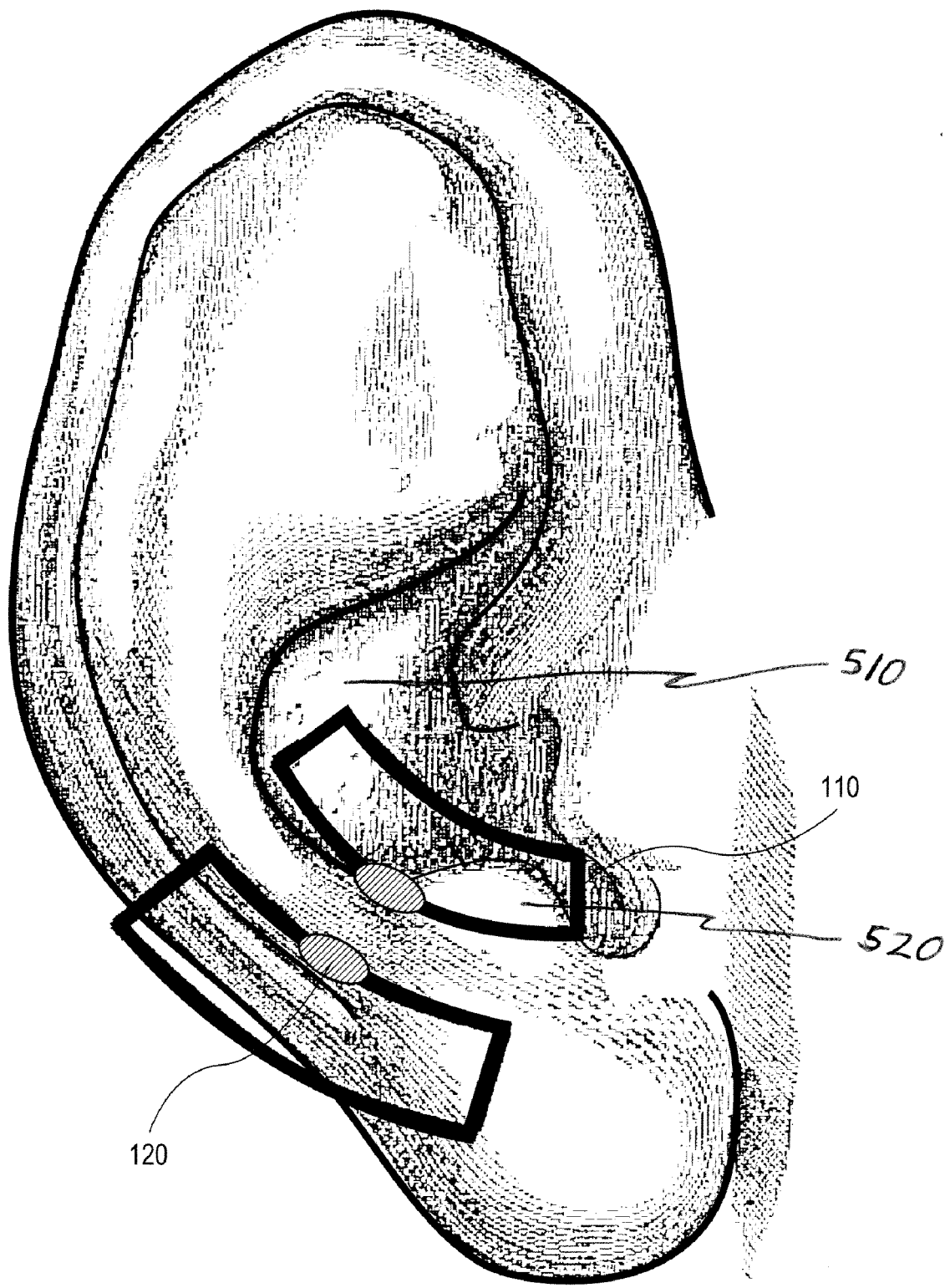
FIG. 5A illustrates a simplified front perspective of the external ear and an approximate placement of block diagrams of the sensor probes according to one embodiment of the disclosure.
Figure 5B:
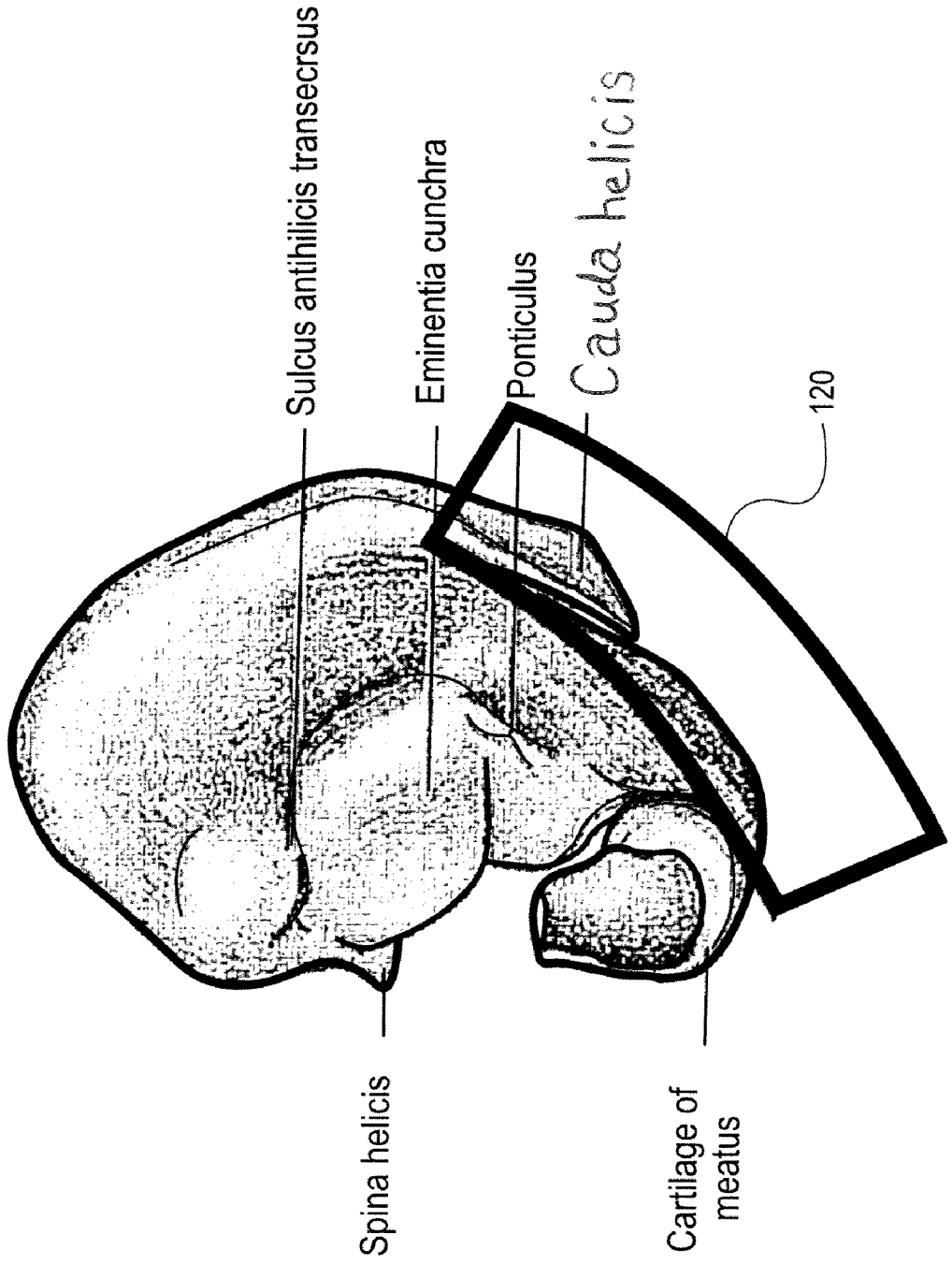
FIG. 5B illustrates a simplified rear perspective of the external ear of FIG. 5A and an approximate placement of a block diagram of the outer sensor probe according to one embodiment of the disclosure.

FIG. 5A illustrates a front perspective of the external ear and an approximate placement of a block diagram of the sensor probes according to one embodiment of the disclosure. In the illustrated embodiment, the inner sensor probe 110 fits within the concha 510 of the ear, near the antitragus 520. The antitragus 520 may provide additional purchase to the inner sensor probe 110 within the concha 510, further securing the inner sensor probe 110. The outer sensor probe 120 fits behind the ear, opposite the inner sensor probe 110. FIG. 5B illustrates a simplified rear perspective of the external ear of FIG. 5A and an approximate placement of a block diagram of the outer sensor probe 120 according to one embodiment of the disclosure. In the illustrated embodiment, the outer sensor probe 120 is located along the cauda helicis. In other embodiments, the inner and outer sensor probes 110, 120 may be placed on other locations of the ear.

Figure 6:
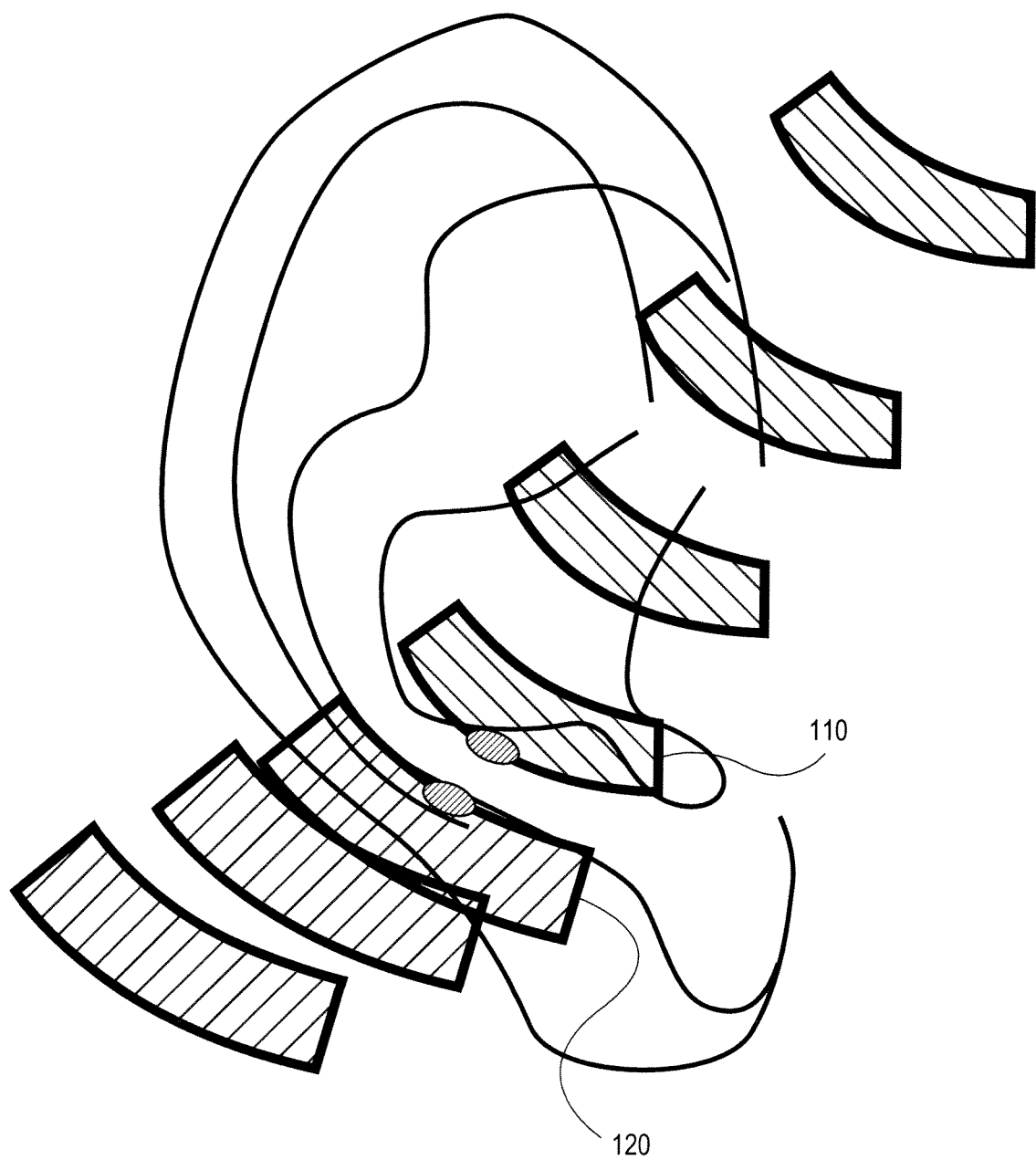
FIG. 6 illustrates a simplified view of the attachment of block diagrams of the inner and outer sensor probes to the external ear according to one embodiment of the disclosure.

FIG. 6 illustrates a simplified view of the attachment of block diagrams of the inner and outer sensor probes 110 and 120 to the external ear according to one embodiment of the disclosure.

Figure 7:
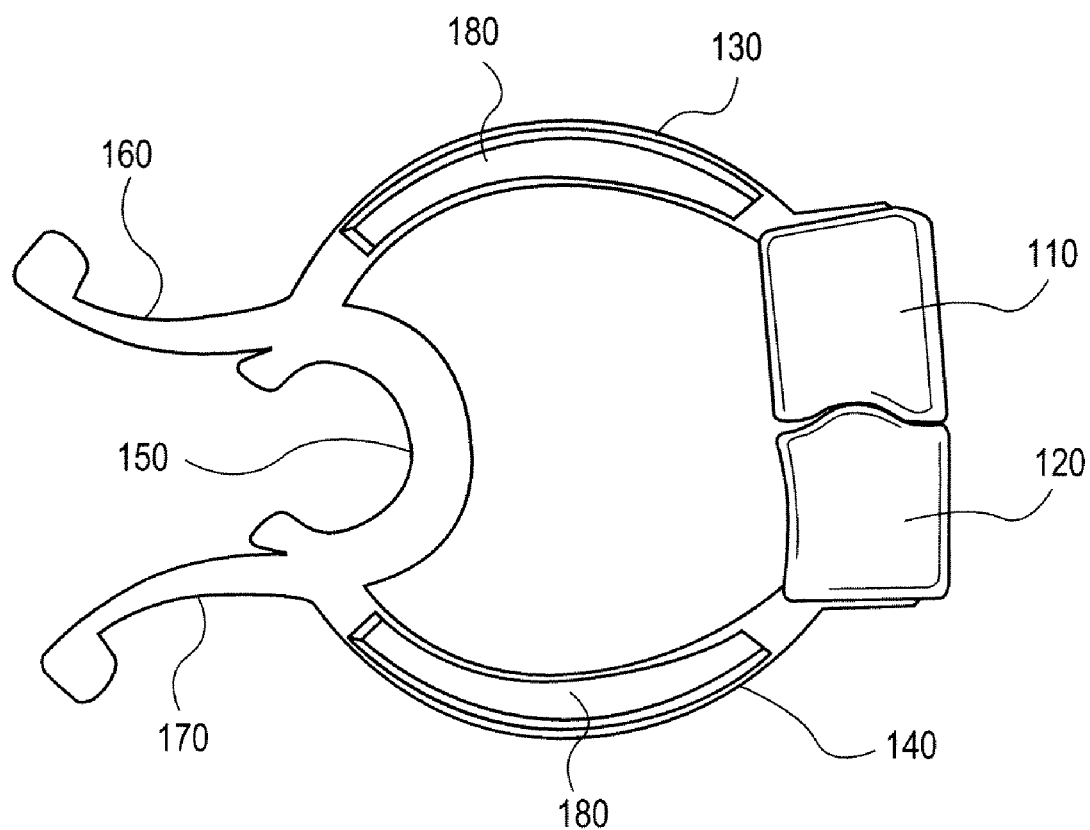
FIG. 7 illustrates another embodiment of the ear sensor assembly where the sensor probes are attached to housings.

FIG. 7 illustrates another embodiment of the ear sensor assembly 100 where sensor probes 110, 120 are attached to housings 180. The upper clip arm 130 and lower clip arm 140 may comprise housings 180 containing electrical components, wires, and/or cables (not shown for the sake of illustration).

Various noninvasive physiological sensor assemblies have been disclosed in detail in connection with various embodiments. These embodiments are disclosed by way of examples only and are not to limit the scope of the claims that follow. One of ordinary skill in the art will appreciate the many variations, modifications and combinations. For example, the various embodiments of the sensor assemblies can be used with sensors that may measure any type of physiological parameter. In various embodiments, the sensor assemblies may be for any type of medical device. Further, the sensor assemblies can be provided in embodiments of various shapes and sizes to account for variations in ear sizes and shapes.

What is claimed is:

1. A noninvasive physiological sensor assembly, the sensor assembly capable of attaching to a tissue site of an ear of a living body, the sensor assembly comprising:
   a plurality of emitters configured to emit light;
   a first housing configured to house and position said plurality of emitters, the first housing having a first contact point configured to curve with the tissue site;
   one or more detectors configured to detect said light after it has been attenuated by tissue of the ear of the living body; and
   a second housing configured to house and position said one or more detectors opposite said plurality of emitters, the second housing having a second contact point configured to curve with the tissue site,
   wherein said first and second housings are configured to allow positioning either said plurality of emitters or said one or more detectors within an ear concha of the living body and the other of said plurality of emitters or said one or more detectors behind the ear of the living body, wherein the first contact point and the second contact point have complimentary shapes.

2. The sensor assembly of claim 1, wherein the first housing comprises a shape smaller than that of the second housing.

3. The sensor assembly of claim 1, wherein the first housing and second housing are configured to conform to cartilaginous structure of the ear.

4. The sensor assembly of claim 1, further comprising a hinge portion mechanically coupling the first housing and the second housing.

5. The sensor assembly of claim 4, wherein the first housing further comprises a first arm, the second housing further comprises a second arm, the first and second arms curving outwardly away from the tissue site.

6. A method of positioning a noninvasive physiological sensor assembly at a tissue site of an ear, the method comprising:
   providing a sensor assembly that includes:
      a first housing including one or more emitters and a first contact point; and
      a second housing including a detector and a second contact point,
      wherein the first housing and second housing are biased toward each other and the first and second contact points have complimentary shapes; and
   releasably attaching the sensor assembly to the tissue site such that the tissue site is disposed between the first housing and second housing, wherein the tissue site comprises a cartilaginous structure of the ear.

7. The method of claim 6, wherein releasably attaching the sensor assembly includes attaching the sensor assembly within a concha of the ear.

8. The method of claim 7, wherein releasably attaching the sensor assembly includes conforming the first housing within the concha of the ear.

9. The method of claim 7, wherein releasably attaching the sensor assembly includes aligning the detector of the second housing behind the ear with the one or more emitters of the first housing.

10. The method of claim 6, wherein releasably attaching the sensor assembly includes conforming the first housing and the second housing to the cartilaginous structure of the ear.

* * * * *